US009861434B2

(12) United States Patent
Kim

(10) Patent No.: US 9,861,434 B2
(45) Date of Patent: Jan. 9, 2018

(54) OPERATION DEVICE FOR PERFORMING PROCEDURE ON LUMEN IN BODY

(71) Applicant: BCM Co., Ltd., Koyang-si (KR)

(72) Inventor: Joon-sang Kim, Incheon-Si (KR)

( * ) Notice: Subject to any disclaimer, the term of this patent is extended or adjusted under 35 U.S.C. 154(b) by 664 days.

(21) Appl. No.: 14/530,831

(22) Filed: Nov. 3, 2014

(65) Prior Publication Data

US 2015/0126989 A1    May 7, 2015

(30) Foreign Application Priority Data

Nov. 6, 2013    (KR) .......................... 10-2013-0133885

(51) Int. Cl.
    *A61B 18/04*     (2006.01)
    *A61B 18/14*     (2006.01)
    *A61B 18/00*     (2006.01)

(52) U.S. Cl.
    CPC ...... *A61B 18/1492* (2013.01); *A61B 18/1445* (2013.01); *A61B 2018/00595* (2013.01); *A61B 2018/00601* (2013.01)

(58) Field of Classification Search
    CPC ............ A61B 18/1445; A61B 18/1492; A61B 2018/00595; A61B 2018/00601
    See application file for complete search history.

(56) References Cited

U.S. PATENT DOCUMENTS

2010/0262180 A1* 10/2010 Danitz ................. A61B 1/0053
                                                      606/205
2011/0295313 A1* 12/2011 Kerr .................... A61B 18/1445
                                                      606/205

FOREIGN PATENT DOCUMENTS

KR       10-0954285      6/2009
KR     10-2012-0139661   12/2012

OTHER PUBLICATIONS

English abstract of 10-2012-0139661.
English abstract of 10-0954285.

* cited by examiner

*Primary Examiner* — George Manuel
(74) *Attorney, Agent, or Firm* — Antonio Ha & U.S. Patent, LLC

(57) ABSTRACT

An operation device for performing a procedure on a lumen in a body comprises: a single protection tube formed of a flexible material; first and second tube members provided in the protection tube; and first and second clamp-type effectors respectively provided at respective front ends of the first and second tube members, wherein operational wires, respectively, are inserted into the first and second tube members to connect the clamp-type effectors positioned at the front ends thereof with first and second manipulation handles positioned at rear ends thereof, wherein the first and second clamp-type effectors are manipulated by moving the operational wires using the first and second manipulation handles in front or rear directions, and wherein electric lines are connected with the first and second clamp-type effectors to electrothermally treat a lesion portion in the body.

5 Claims, 8 Drawing Sheets

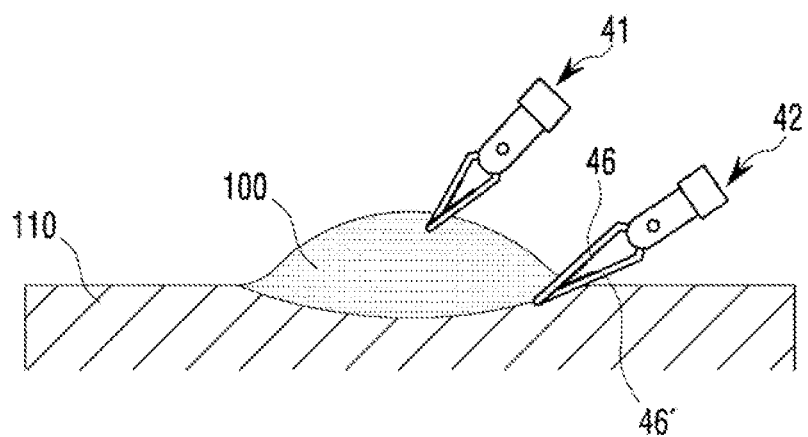
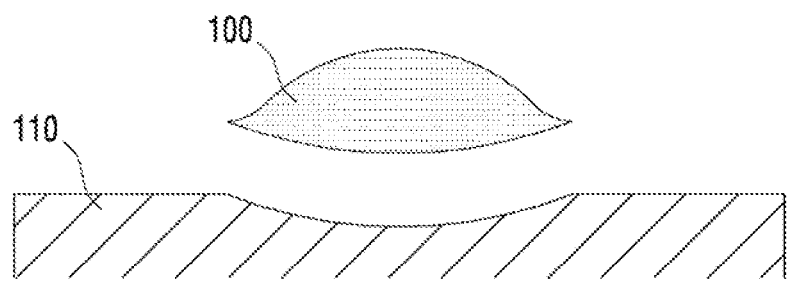

OPERATION DEVICE FOR PERFORMING PROCEDURE ON LUMEN IN BODY

CROSS-REFERENCE TO RELATED APPLICATIONS

This patent application claims priority under 35 U.S.C. § 119 to Korean Patent Application No. 10-2013-0133885 filed on Nov. 6, 2013 in the Korean Intellectual Property Office, the disclosure of which is incorporated by reference herein in its entirety.

TECHNICAL FIELD

Embodiments of the present invention relate to an operation device for performing a procedure on a lumen in the body, and more specifically, to an operation device for performing a procedure on a lumen in the body, which uses two (first and second) clamp-type effectors connected with electric lines to primarily incise a lesion portion, such as tumor on a mucosal tumor in the body, or to be connected with a stent for thermal treatment inserted in a lumen in the body to perform thermal treatment, thereby allowing for simple and efficient procedure on the lesion tissue.

DISCUSSION OF RELATED ART

In recent years, non-surgical treatment, such as electric (or high-frequency) incision, is being widely practiced to incise or cauterize a lesion portion such as a mucosal tumor in the body.

In such electrothermal treatment, an operator inserts an operation device for performing a procedure on a lumen in the body into the lesion portion while observing the lesion portion through an endoscope and allowing electricity (or high-frequency wave) to flow through the operation device to thereby cauterize or incise the lesion portion.

Korean Patent No. 10-954285 discloses an operation device for performing a procedure on a lumen in the body, which allows an electric (or high-frequency) current to flow through a needle or knife inserted through an endoscope into a lesion portion in the body and cauterizes or cuts away the lesion portion by the needle or knife.

Korean Patent Application No. 10-2012-7004969 discloses removing a lesion portion by opening and closing a clamp-type effector while enabling an electric (high-frequency) current to flow through the effector.

In such conventional operation devices for performing a procedure on a lumen in the body, a single needle or knife or a single effector is inserted into a lesion portion that is then incised or cauterized by the needle, knife, or effector to achieve treatment effects. As such, the conventional treatment adopts a single means to perform the treatment and thus cannot precisely or effectively remove the lesion tissue from the normal tissues.

Further, the conventional operation devices for performing a procedure on a lumen in the body, which employ the conventional effectors, have complicated effector manipulation structure, thus rendering it difficult for the user to conduct a procedure therewith.

SUMMARY

The present invention has been designed to address the issues of the related art, and an embodiment of the present invention is to provide an operation device for performing a procedure on a lumen in the body, and more specifically, to an operation device for performing a procedure on a lumen in the body, which uses two (first and second) clamp-type effectors connected with electric lines to primarily incise a lesion portion, such as a mucosal tumor in the body, or to be connected with a stent for thermal treatment inserted into a lumen in the body to perform thermal treatment, thereby allowing for simple and efficient procedure on the lesion tissue.

For example, the present invention aims to simply and precisely incise a lesion portion such as a mucosal tumor in the body from a normal tissue with the second clamp-type effector, with the lesion portion pulled and elongated by the first clamp-type effector or to selectively connect the first and second clamp-type effectors to a stent for thermal treatment placed in a lesion portion in a lumen of the body to electrothermally cauterize the lesion portion in a simple way.

The present invention aims to more effectively conduct an incision operation by forming the second clamp-type effector used to incise the lesion portion to be longer than the first clamp-type effector used for clamping.

The present invention aims to simply perform a procedure by manipulation of the first and second clamp-type effectors through a simple configuration of the first and second manipulation handles for manipulating the first and second clamp-type effectors.

The present invention is characterized by an operation device for performing a procedure on a lumen in a body, comprising: a single protection tube formed of a flexible material; first and second tube members and provided in the protection tube; first and second clamp-type effectors and respectively provided at respective front ends of the first and second tube members, wherein operational wires, respectively, are inserted into the first and second tube members to connect the clamp-type effectors positioned at the front ends thereof with first and second manipulation handles positioned at rear ends thereof, wherein the first and second clamp-type effectors are manipulated by moving the operational wires using the first and second manipulation handles in front or rear directions, and wherein electric lines are connected with the first and second clamp-type effectors to electrothermally treat a lesion portion in the body.

The present invention is characterized in that the electric lines respectively connected with the first and second clamp-type effectors are connected to respective electric ports of the first and second manipulation handles via an inside of the protection tube, and connection jacks of an electric oscillator for medical purpose are selectively inserted and connected into the electric ports to selectively supply power.

The present invention is characterized in that the first and second clamp-type effectors are configured so that the second clamp-type effector connected with an electric line to function to incise the lesion tissue out of a normal tissue by electric heat is longer than the first clamp-type effector functioning as a clamp to hold the lesion portion, such as a mucosal tumor, in the body.

The present invention is characterized in that the first and second manipulation handles each include a holding part having a finger hole through which a thumb is inserted at a rear side thereof, a body coupled with a front part of the holding part and having an inner space through which the first or second tube member is inserted, and a bobbin-type operational piston connected with the body to be movable along an outer surface of the body in front and rear directions, with an index finger and a middle finger placed thereon for holding, and wherein an end of the operational wire is connected with the operational piston so that the front-and-rear directional movement of the operational wire may be adjusted by the operational piston.

According to the present invention, first and second tube members respectively coupled with two clamp-type effector respectively connected with electric lines in a single protection tube, operational wires, and first and second manipulation handles are collectively configured to use the two clamp-type effectors to electrothermally incise a lesion portion, such as a mucosal tumor, in the body out of a normal tissue or to connect the same to a stent for thermal treatment placed in a lumen of the body to perform a thermal treatment procedure.

In particular, a lesion portion, such as a mucosal tumor, in the body may be electrothermally incised in a simple and precise manner from a normal tissue by the second clamp-type effector, with the lesion portion pulled and elongated by the first clamp-type effector, or the first and second clamp-type effectors are selectively connected to a stent for thermal treatment placed in a lesion portion in a lumen of the body to electrothermally cauterize the lesion portion in a simple way.

Further, the second clamp-type effector used to incise a lesion tissue is formed to be longer than the first clamp-type effector primarily used as a clamp, thus leading to a better incision operation. Further, the configuration of the first and the second manipulation handles is simplified, thus facilitating to perform a procedure by manipulating the first and second clamp-type effectors.

BRIEF DESCRIPTION OF DRAWINGS

A more complete appreciation of the present disclosure and many of the attendant aspects thereof will be readily obtained as the same becomes better understood by reference to the following detailed description when considered in connection with the accompanying drawings, wherein.

DETAILED DESCRIPTION OF EMBODIMENTS

Figure 1:
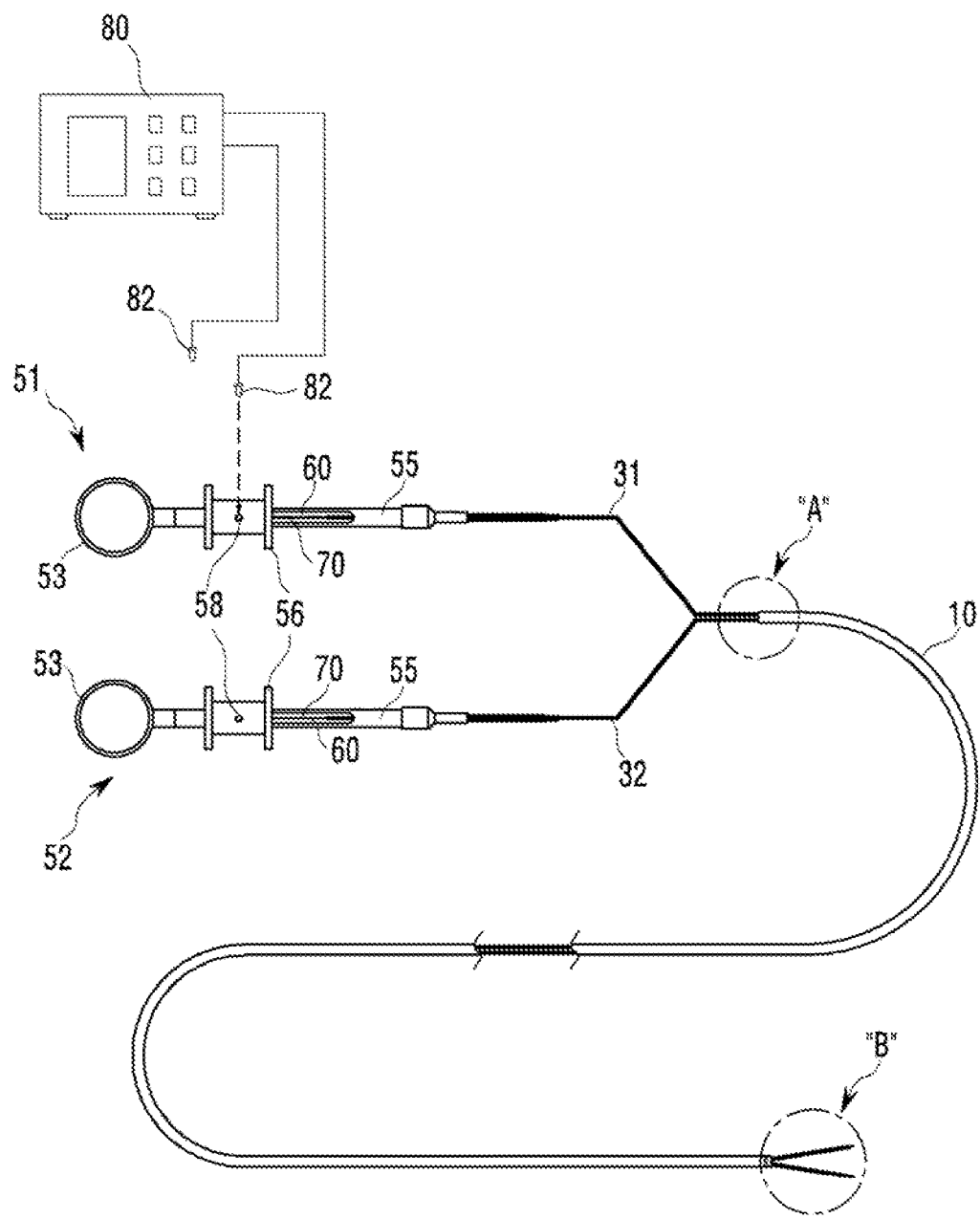
FIG. 1 is a front view illustrating an overall configuration of a device according to an embodiment of the present invention.
Figure 2:
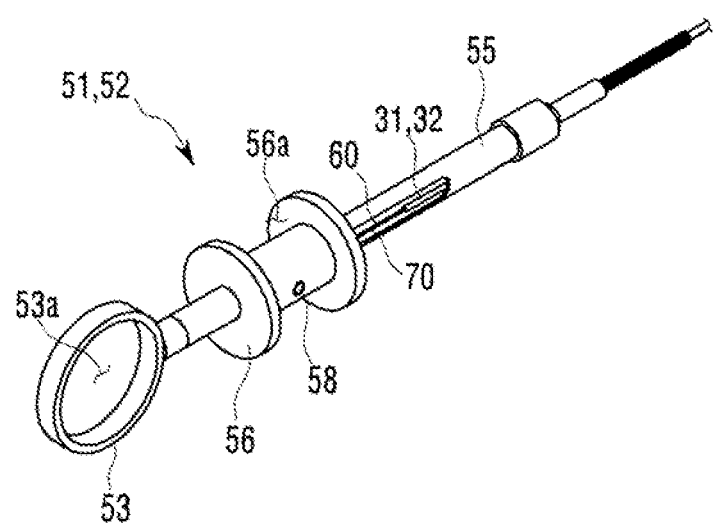
FIG. 2 is a perspective view illustrating a manipulation handle as shown in FIG. 1.
Figure 3:
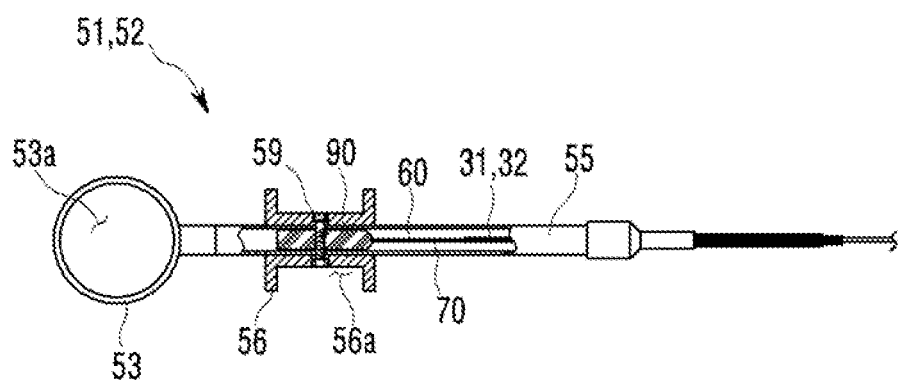
FIG. 3 is a cross-sectional view of FIG. 2.
Figure 4:
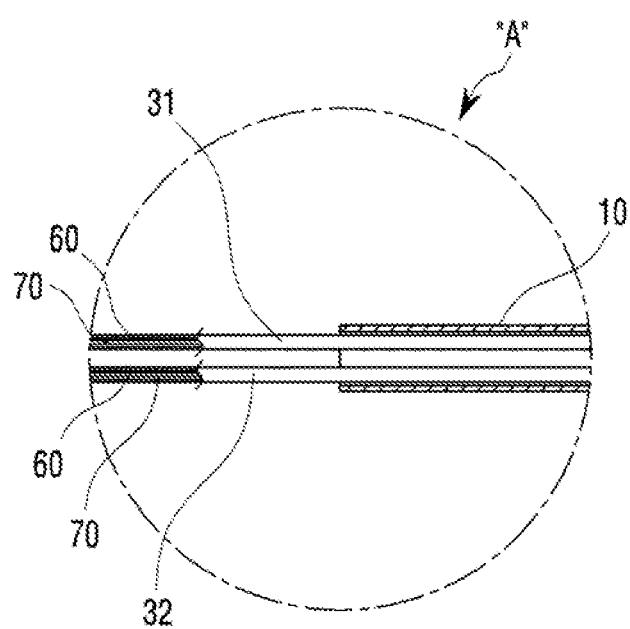
FIG. 4 is an expanded cross-sectional view illustrating area "A" of FIG. 1.
Figure 5:
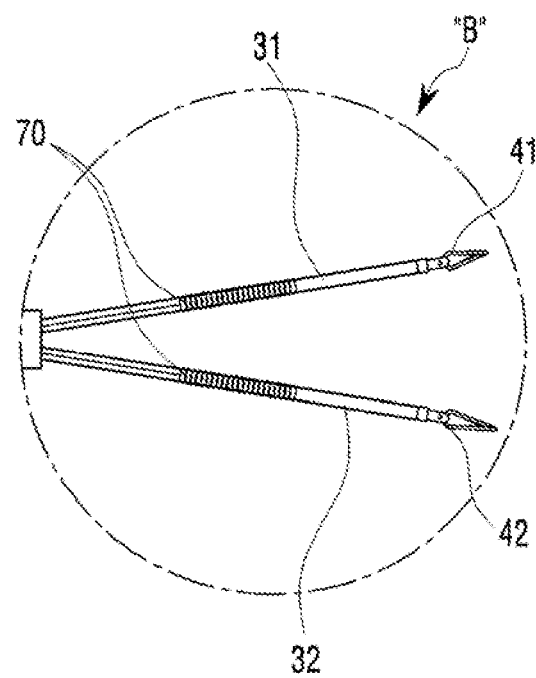
FIG. 5 is an expanded cross-sectional view illustrating area "B" of FIG. 1.
Figure 6:
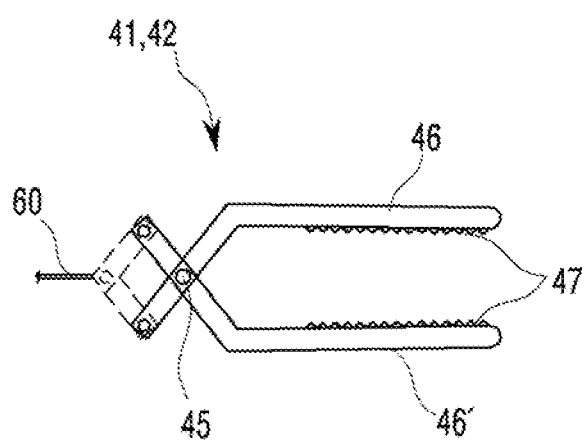
FIGS. 6 and 7 are front views respectively illustrating a state in which a first or second clamp-type effector is opened and a state in which the first or second clamp-type effector is closed.
Figure 7:
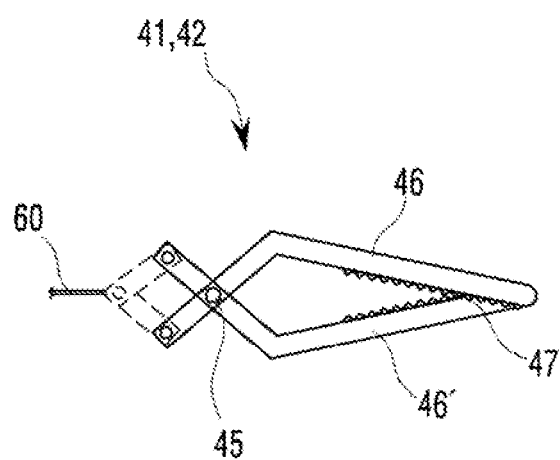
Figure 8A:
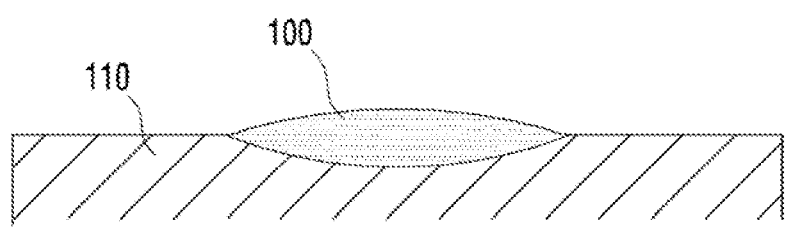
FIGS. 8A, 8B. 8C, 8D, and 9 are front views illustrating examples of using a device according to an embodiment of the present invention.
Figure 8B:
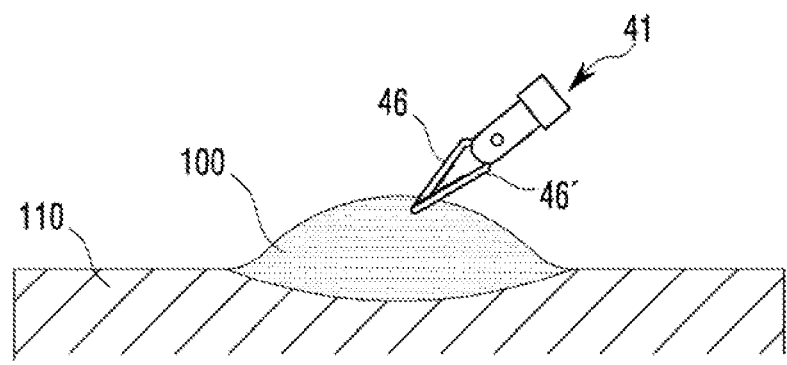

Hereinafter, exemplary embodiments of the present invention will be described in detail with reference to the accompanying drawings. The present invention, however, may be modified in various different ways, and should not be construed as limited to the embodiments set forth herein. As used herein, the singular forms "a," "an," and "the" are intended to include the plural forms as well, unless the context clearly indicates otherwise. It will be understood that when an element or layer is referred to as being "on," "connected to," "coupled to," or "adjacent to" another element or layer, it can be directly on, connected, coupled, or adjacent to the other element or layer, or intervening elements or layers may be present.

According to an embodiment of the present invention, an operation device for performing a procedure on a lumen in the body includes a single protection tube 10 formed of a flexible material, first and second tube members 31 and 32 provided in the protection tube 10, first and second clamp-type effectors 41 and 42 respectively provided at respective front ends of the first and second tube members 31 and 32.

Operational wires 60, respectively, are inserted into the first and second tube members 31 and 32 to connect the clamp-type effectors 41 and 42 positioned at the front ends thereof with first and second manipulation handles 51 and 52 positioned at rear ends thereof. The first and second clamp-type effectors 41 and 42 are manipulated by moving the operational wires 60 using the first and second manipulation handles 51 and 52 in front or rear directions, and electric lines are connected with the first and second clamp-type effectors 41 and 42 to electrothermally treat a lesion portion in the body.

The first and second clamp-type effectors 41 and 42 each include left and right jaws 46 and 46' crossing each other in the shape of the letter "X," and a pivot pin 45 coupling the left and right jaws 46 and 46' with each other. Each of the left and right jaws 46 and 46' includes a serrated fixed part 47 therein. Rear ends of the left and right jaws 46 and 46' are connected with the operational wires 60, and the left and right jaws 46 and 46' may be opened or closed with respect to the pivot pin 45, like a clamp, by adjusting the front-and-rear directional movement.

Further, electric lines 70, respectively, are connected with the first and second clamp-type effectors 41 and 42 to selectively supply power to either or both of the first and second clamp-type effectors 41 and 42.

For example, the electric lines 70 connected with the first and second clamp-type effectors 41 and 42 are connected to respective electric ports 58 of the first and second manipulation handles 51 and 52 via the inside of the protection tube 10, and connection jacks 82 of an electric oscillator 80 for medical purpose are selectively inserted and connected into the electric ports 80 to supply power thus to perform electrothermal treatment.

Further, the first and second clamp-type effectors 41 and 42 may be used to perform an incision on a lesion portion, such as a mucosal tumor in the body, using electric heat or may be connected with a stent provided in a lumen in the body for thermal treatment. In particular, the second clamp-type effector 42 functioning to incise the lesion tissue out of a normal tissue by electricity may be preferably longer than the first clamp-type effector 41 functioning as a clamp to hold the lesion portion such as a mucosal tumor in the body for an incision procedure using electric heat.

The first and second manipulation handles 51 and 52 each include a holding part 53 having a holding hole 53a through which a thumb is inserted at a rear side thereof, a body 55 coupled with a front part of the holding part 53 and having an inner space 55a through which the first or second tube member 31 or 32 is inserted, and a bobbin-type operational piston connected with the body 55 to be movable along an outer surface of the body in front and rear directions, with an index finger and a middle finger placed on an outer insertion groove 56a for holding. An end of the operational wire 60 is connected with the operational piston so that the front-and-rear directional movement of the operational wire 60 may be adjusted by the operational piston.

The reference numeral 59 indicates an assembling bolt for assembling a fixture 70 connected with ends of the operational wire 60 and the electric line 70 into the operational piston 56.

An operation and action of the above-described operation device is described according to an embodiment of the present invention.

An electrical incision procedure on a lesion portion such as a mucosal tumor in the body is first described. As shown in FIGS. 8A, 8B, 8C, and 8D, the first and second clamp-type effectors 41 and 42 positioned at front ends of the first and second tube members 31 and 32 in the protection tube 10 are inserted into a lesion portion 100 such as a mucosal tumor in the body.

In such state, the first and second manipulation handles 51 and 52 for manipulating the first and second clamp-type effectors 41 and 42 are held by inserting the thumbs into the holding holes 53a of the holding parts 53 and placing the index and middle fingers on the outer insertion grooves 56a of the operational pistons 56.

In this case, the connection jack 82 of the electric oscillator 80 is connected to the electric port 58 of the second manipulation handle 52 corresponding to the second clamp-type effector 42 so that power is supplied through only the electric line 70 connected with the second clamp-type effector 42 to perform an electrothermal incision procedure using the second clamp-type effector 42.

This is descried in greater detail.

The operational piston 56 of the first manipulation handle 51 connected with the first clamp-type effector 41 is pushed from the body 55 to move the operational wire 60 of the first tube member 31 forwards, so that the first clamp-type effector 41 positioned at the front end of the first tube member 31 is opened.

For example, the operational wire 60 pushes the rear ends of the left and right jaws 46 and 46' of the first clamp-type effector 41 that cross each other in the "X" shape so that the front sides of the left and right jaws 46 and 46' are opened from side to side with respect to the pivot pin 45.

In such situation, the first clamp-type effector 41 is placed on the center of the lesion portion 100.

In such state, the operational piston 56 of the first manipulation handle 51 is pulled from the body 55 to move the operational wire 60 inside the first tube member 31 rearwards, so that the first clamp-type effector 41 positioned at the front end of the first tube member 31 is closed, thus holding the center of the lesion portion 100 like a clamp.

For example, the operational wire 60 pulls the rear ends of the left and right jaws 46 and 46' of the first clamp-type effector 41 that cross each other in the "X" shape so that the front sides of the left and right jaws 46 and 46' are closed with respect to the pivot pin 45.

In this case, the lesion portion 100 is effectively held by the serrated fixed parts 47 formed on insides of the left and right jaws 46 and 46'.

Under such situation, the portion between the lesion portion 100 and the normal tissue 110 is electrothermally incised by the second clamp-type effector 42, with the lesion portion 100 pulled and elongated by the first clamp-type effector 41.

In other words, like the above-described first clamp-type effector 41, the second clamp-type effector 42 is opened and closed by pulling and pushing the operational piston 56 of the second manipulation handle 52 of the second clamp-type effector 42 from the body 55 to thereby moving the operational wire 60 inside the second tube member 32 in the front and rear directions, while the portion between the normal tissue and the lesion portion 100 is incised by electric heat.

In particular, the second clamp-type effector 42 functioning to incise the lesion tissue out of the normal tissue by electric heat is formed to be longer than the first clamp-type effector 41 functioning as a clamp holding the lesion portion, and thus, electrothermal incision on the portion between the normal tissue 110 and the lesion portion 100 may be more quickly and effectively performed.

As such, the lesion portion 100 may be completely removed from the normal tissue 110 by performing an electrothermal incision along the portion between the normal tissue 110 and the lesion portion 100 by the second clamp-type effector 42, with the center of the lesion portion 100 pulled and elongated by the first clamp-type effector 41.

Accordingly, the lesion portion 100 such as a mucosal tumor in the body, may be simply and effectively removed by electric heat and the first and second clamp-type effectors, not a single effector as in the conventional art.

Figure 9:
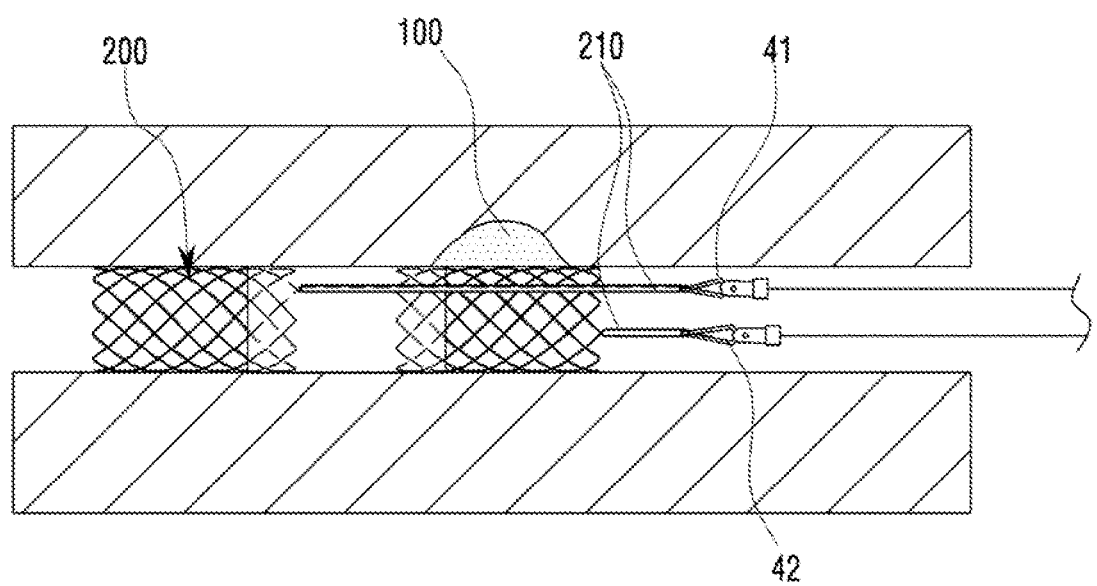

Next, a process of performing thermal treatment on the lesion tissue after inserting a stent into the lesion portion 100 that is being stenosed or has been stenosed in a lumen of the body to expand the lesion portion is described. As shown in FIG. 9, the above-described first and second clamp-type effectors 41 and 42 for body insertion are connected with power lines 210 of a stent 200 for thermal treatment that is inserted into the lesion portion.

The operational pistons 56 of the first and second manipulation handles 51 and 52 of the first and second clamp-type effectors 41 and 42 are pushed from the bodies 55 to move the operational wires 60 of the first and second tube members 31 and 32 forwards, so that the first and second clamp-type effectors 41 and 42 positioned at the front ends of the first and second tube member 31 and 32 are opened and to place the first and second clamp-type effectors 41 and 42 to the power lines 210 of the stent 200.

In such state, the operational pistons 56 of the first and second manipulation handles 51 and 52 are pulled from the bodies 55 to move the operational wires 60 of the first and second tube members 31 and 32 rearwards, so that the first and second clamp-type effectors 41 and 42 positioned at the front ends of the first and second tube member 31 and 32 are closed to hold the power lines 210 of the stent 200.

In such situation, to perform thermal treatment on the portion where the stent 200 connected with the first and second clamp-type effectors 41 and 42, the connection jacks 82 of the electric oscillator 80 are selectively inserted and connected to the electric ports 58 of the first and second manipulation handles 51 and 52, and power is supplied to the electric lines 70 connected with the first and second clamp-type effectors 41 and 42, thereby electrothermally cauterizing the lesion portion 100 on the stent 200 for thermal treatment connected with the first and second clamp-type effectors 41 and 42.

As such, according to the present invention, first and second tube members respectively coupled with two (i.e., first and second) clamp-type effector respectively connected with electric lines in a single protection tube, operational wires, and first and second manipulation handles are collectively configured to use the two clamp-type effectors. A lesion portion such as a mucosal tumor in the body is electrothermally incised out of a normal tissue by the second clamp-type effector, with the lesion portion pulled and elongated by the first clamp-type effector. Or, the first and second clamp-type effectors are selectively connected to a stent for thermal treatment, which is provided into a lesion portion in a lumen of the body, so that the lesion portion may be cauterized by electric heat. Accordingly, such procedure may be simply and effectively performed.

While the present invention has been shown and described with reference to exemplary embodiments thereof, it will be apparent to those of ordinary skill in the an that various changes in form and detail may be made thereto without departing from the spirit and scope of the present invention as defined by the following claims.

What is claimed is:

1. An operation device for performing a procedure on a lumen in a body, comprising:
    a single protection tube formed of a flexible material;
    first and second tube members provided in the protection tube; and
    first and second clamp-type effectors respectively provided at respective front ends of the first and second tube members, wherein operational wires, respectively, are inserted into the first and second tube members to connect the clamp-type effectors positioned at the front ends thereof with first and second manipulation handles positioned at rear ends thereof, wherein the first and second clamp-type effectors are manipulated by moving the operational wires using the first and second manipulation handles in front or rear directions, and wherein electric lines are connected with the first and second clamp-type effectors to electrothermally treat a lesion portion in the body, wherein the first and second manipulation handles each include a holding part having a finger hole through which a thumb is inserted at a rear side thereof, a body coupled with a front part of the holding part and having an inner space through which the first or second tube member is inserted, and a bobbin-type operational piston connected with the body to be movable along an outer surface of the body in front and rear directions, with an index finger and a middle finger placed thereon for holding, and wherein an end of the operational wire is connected with the operational piston so that the front-and-rear directional movement of the operational wire may be adjusted by the operational piston.

2. The operation device of claim 1, wherein the electric lines respectively connected with the first and second clamp-type effectors are connected to respective electric ports of the first and second manipulation handles via an inside of the protection tube, and connection jacks of an electric oscillator for medical purpose are selectively inserted and connected into the electric ports to selectively supply power.

3. An operation device for performing a procedure on a lumen in a body, comprising:
    a single protection tube formed of a flexible material;
    first and second tube members provided in the protection tube; and
    first and second clamp-type effectors respectively provided at respective front ends of the first and second tube members, wherein operational wires, respectively, are inserted into the first and second tube members to connect the clamp-type effectors positioned at the front ends thereof with first and second manipulation handles positioned at rear ends thereof, wherein the first and second clamp-type effectors are manipulated by moving the operational wires using the first and second manipulation handles in front or rear directions, and wherein electric lines are connected with the first and second clamp-type effectors to electrothermally treat a lesion portion in the body, wherein the first and second clamp-type effectors each include left and right jaws crossing each other in the shape of the letter "X," and a pivot pin coupling the left and right jaws with each other, each of the left and right jaws including a serrated fixed part therein, and wherein rear ends of the left and right jaws are connected with the operational wires, and the left and right jaws may be opened or closed with respect to the pivot pin, like a clamp, by adjusting the front-and-rear directional movement.

4. An operation device for performing a procedure on a lumen in a body, comprising:
    a single protection tube formed of a flexible material;
    first and second tube members provided in the protection tube; and
    first and second clamp-type effectors respectively provided at front ends of the first and second tube members, wherein operational wires, respectively, are inserted into the first and second tube members to connect the clamp-type effectors positioned at the front ends thereof with first and second manipulation handles positioned at rear ends thereof, wherein the first and second clamp-type effectors are manipulated by moving the operational wires using the first and second manipulation handles in front or rear directions, wherein the first and second clamp-type effectors are configured so that the second clamp-type effector connected with an electric line to function to incise the lesion tissue out of a normal tissue by electric heat is longer than the first clamp-type effector functioning as a clamp to hold the lesion portion in the body, wherein the first and second manipulation handles each include a holding part having a finger hole through which a thumb is inserted at a rear side thereof, a body coupled with a front part of the holding part and having an inner space through which the first or second tube member is inserted, and a bobbin-type operational piston connected with the body to be movable along an outer surface of the body in front and rear directions, with an index finger and a middle finger placed thereon for holding, and wherein an end of the operational wire is connected with the operational piston so that the front-and-rear directional movement of the operational wire may be adjusted by the operational piston.

5. The operation device of claim 4, wherein the first and second clamp-type effectors each include left and right jaws crossing each other in the shape of the letter "X," and a pivot pin coupling the left and right jaws with each other, wherein each of the left and right jaws includes a serrated fixed part therein, and wherein rear ends of the left and right jaws are connected with the operational wires, and the left and right jaws may be opened or closed with respect to the pivot pin, like a clamp, by adjusting the front-and-rear directional movement.

* * * * *